(12) United States Patent
Johnston et al.

(10) Patent No.: US 11,090,160 B2
(45) Date of Patent: Aug. 17, 2021

(54) ORTHOGNATHIC IMPLANT ASSEMBLY AND METHOD OF USE

(71) Applicant: KLS Martin, Inc., Jacksonville, FL (US)

(72) Inventors: Thomas S. Johnston, Jacksonville, FL (US); Tirth Patel, Jacksonville, FL (US)

(73) Assignees: KLS MARTIN, INC., Jacksonville, FL (US); KLS MARTIN, LP, Jacksonville, FL (US)

( * ) Notice: Subject to any disclaimer, the term of this patent is extended or adjusted under 35 U.S.C. 154(b) by 170 days.

(21) Appl. No.: 16/054,745

(22) Filed: Aug. 3, 2018

(65) Prior Publication Data

US 2019/0038414 A1 Feb. 7, 2019

Related U.S. Application Data

(60) Provisional application No. 62/540,820, filed on Aug. 3, 2017.

(51) Int. Cl.
*A61F 2/28* (2006.01)
*A61F 2/30* (2006.01)
*A61B 17/80* (2006.01)

(52) U.S. Cl.
CPC ........ *A61F 2/2803* (2013.01); *A61B 17/8071* (2013.01); *A61F 2/2875* (2013.01);
(Continued)

(58) Field of Classification Search
CPC ................. A61F 2/2803; A61F 2/2875; A61F 2002/2889; A61F 2002/3096;
(Continued)

(56) References Cited

U.S. PATENT DOCUMENTS

| 9,028,498 B2 * | 5/2015 | Hershgold | ......... A61B 17/8042 606/71 |
| 2007/0055254 A1 * | 3/2007 | Ihde | ....................... A61C 8/001 606/71 |

(Continued)

FOREIGN PATENT DOCUMENTS

| CN | 102335033 A | 2/2012 |
| DE | 4018273 A1 | 1/1991 |

*Primary Examiner* — Brian A Dukert
*Assistant Examiner* — Amanda M Barkan
(74) *Attorney, Agent, or Firm* — Thomas C. Saitta (57) ABSTRACT

A maxillofacial orthognathic fixation implant assembly and its method of production and use, the implant being an assembly of an upper anchor implant member, a lower anchor implant member and at least one bridging implant member, the anchor implant members being adapted to be securely mounted to a maxilla and the at least one bridging implant member being adapted to connect the upper anchor implant member to the lower anchor implant member in a fixed and rigid manner. With the anchor implant members affixed to the maxilla and the maxilla surgically separated between the upper and lower anchor implant members to create a lower portion detached an upper portion, the at least one bridging implant member is connected between the upper and lower anchor implant members to secure and maintain the lower portion of the maxilla in a desired post-operative position relative to the upper portion of the maxilla.

11 Claims, 6 Drawing Sheets

(52) U.S. Cl.
CPC ...... *A61F 2/30942* (2013.01); *A61B 17/8085* (2013.01); *A61F 2002/2889* (2013.01); *A61F 2002/3096* (2013.01)

(58) Field of Classification Search
CPC . A61B 17/8071; A61B 17/80; A61B 17/8085; A61B 17/16; A61B 17/17; A61B 17/7059
See application file for complete search history.

(56) References Cited

U.S. PATENT DOCUMENTS

2012/0277749 A1\* 11/2012 Mootien .............. A61B 17/666
606/70
2015/0018829 A1 1/2015 Woodburn, Sr. et al.

\* cited by examiner

ORTHOGNATHIC IMPLANT ASSEMBLY AND METHOD OF USE

BACKGROUND OF THE INVENTION

This invention relates generally to the field of maxillofacial orthognathic surgical implants and techniques used in the correction of malformations of the maxilla and/or mandible, and more particularly relates to such implants and techniques wherein a lower portion of the maxilla is surgically separated from the upper portion of the maxilla, such that the lower portion is realigned relative to the upper portion to produce a more desirable facial configuration. Even more particularly, the invention relates to such implants and techniques wherein the implants are customized to better conform to the surface configuration of the maxilla, the customization utilizing 3-D imaging to determine the optimal size and configurations for the implants.

The term orthognathic comes from the Greek words "orthos" meaning straighten and "gnathic" meaning of or related to the jaw. Orthognathic surgery may be indicated in order to make biting and chewing easier and improve chewing overall, correct problems with swallowing or speech, minimize excessive wear and breakdown of the teeth, correct bite fit or jaw closure issues, correct facial imbalance (asymmetry), such as small chins, underbites, overbites and cross bites, improve the ability of the lips to fully close comfortably, relieve pain caused by temporomandibular joint (TMJ) disorder and other jaw problems, repair facial injury or birth defects, or provide relief for obstructive sleep apnea.

In a basic maxillary orthognathic procedure, the surgeon determines the desired post-operative configuration for the maxilla, performs an osteotomy to separate a lower portion of the maxilla from the upper portion, repositions the lower portion relative to the upper portion, and affixes in the lower portion in the realigned position by attaching rigid implants, also known as fixation plates, bone plants or the like, to the lower portion and the upper portion, the fixation implants bridging the osteotomy gap and fastened to the upper and lower portions using mechanical fasteners, i.e., bone screws. The lower portion may be translated, rotated, angled, etc. in one or multiple directions. In the final fixed alignment the lower portion may be spaced from the upper portion across the osteotomy, such as for example if the lower portion is to be brought forward or down from the upper portion, or a portion of the bone may be removed from the upper and/or lower portion of the maxilla in order to shorten the overall configuration of the post-operative maxilla.

More recently, the use of 3-D imagery such as X-ray or CT-scanning, is being utilized in the procedure to better ascertain the desired post-operative configuration and to provide a method for producing customized fixation implants. A pre-operative 3-D image of the maxillary bone is produced and the surgeon, using dedicated software, is able to perform a virtual osteotomy and then manipulate the lower portion of the maxilla relative to the upper portion to produce a virtual image of the desired post-operative configuration for the maxilla. Customized virtual implants may then be created that are shaped and configured to match the surface configuration of the maxilla over the areas where the implant will contact the bone surface. Likewise, the portions of the customized virtual implants extending across the osteotomy may be shaped and configured such that once the implant is affixed to the lower and upper portions of the maxilla, the lower portion resides in the desired realigned position relative to the upper portion. An actual implant for use in surgery is then manufactured to match the specifications of the virtual implant.

It is an object of this invention to provide an improved maxillofacial orthognathic method and related implants, the implants comprising an assembly of anchor implant members and bridging implant members which ensure accurate placement and fixation of the implants and proper post-osteotomy alignment of the bone segments.

SUMMARY OF THE INVENTION

The invention is an orthognathic fixation implant assembly and the method of utilizing the implant assembly, wherein the implant assembly comprises an upper anchor implant member adapted for affixation to the upper portion of a maxilla, a lower anchor implant member adapted for affixation to the lower portion of a maxilla, and at least one bridging or cross-brace implant member adapted to connect the upper and lower anchor implant members in a fixed and rigid manner, the at least one bridging implant member being attachable to and detachable from the upper and lower anchor implant members by mechanical fasteners. The size and 3-D configuration of the lower anchor, upper anchor and bridging implant members are determined using 3-D imaging to create virtual lower and upper anchor implant members conforming to the surface configuration of the maxilla and to create virtual bridging implant members properly curved, bent, twisted or otherwise configured to be attachable to the lower and upper anchor implant members, such that a lower portion of the maxilla separated from the upper portion is properly realigned once actual implant lower and upper anchor implant members, manufactured to match the virtual implant members, have been affixed to the maxilla and connected across an osteotomy gap by actual bridging implant members, likewise manufactured to match the virtual implant members.

After the implant members have been manufactured based on the 3-D imaging, in a first method embodiment, the upper anchor implant members are affixed to the upper portion of the maxilla using mechanical fasteners, e.g., bone screws, and the lower anchor implant members are affixed to the lower portion of the maxilla using mechanical fasteners, e.g., bone screws. An osteotomy is performed between the upper and lower anchor implant members, thereby separating the lower portion of the maxilla from the upper portion. The bridging implant members are then connected between the upper anchor implant members and the lower anchor implant members, the bridging implant members extending across the osteotomy gap to secure and maintain the lower portion of the maxilla in a fixed position relative to the upper portion of the maxilla, the size and configuration of the bridging implant members resulting in the desired post-operative configuration for the lower portion of the maxilla relative to the upper portion of the maxilla. Alternatively, the method may comprise the steps of attaching the upper anchor implant members, performing the osteotomy and then attaching the lower anchor implant members, or may comprise the steps of attaching the lower anchor implant members, performing the osteotomy and then attaching the upper anchor implant members.

The upper or lower anchor implant members, alone or together, may be configured so as to define the osteotomy cutting line, such that the anchor implant member or members may be used as a marking guide or even a cutting guide.

In an alternative embodiment, one or more pre-osteotomy bridging implant members may be temporarily attached to the upper and lower anchor implant members prior to affixation to the bone, the pre-osteotomy bridging implant members being an alignment member configured for proper placement of the anchor implant members prior to making the osteotomy cut. The pre-osteotomy bridging implant member is configured based on the pre-osteotomy configuration of the maxillofacial area. Once the anchor implant members are affixed to the bone, the pre-osteotomy bridging implant member is removed, the osteotomy cut is performed and one or more post-osteotomy bridging implant members are affixed between the anchor implant members, the post-osteotomy bridging implant members being configured based on the translated post-operative desired configuration of the maxillofacial area.

In another embodiment, the upper and lower anchor implant members are initially formed with thin connecting members extending between the two, such that proper pre-osteotomy positioning of the anchor implant members is easier to achieve. After the anchor implant members are attached to the bone, the connecting members are cut and removed. Furthermore, a marking or cutting guide may be affixed to one of the anchor implant members by a thin connecting member, such that marking or cutting guide may be utilized before or after separating the anchor implant members, the guide being removed after its use.

Alternatively summarized, the invention is a maxillofacial orthognathic fixation implant assembly comprising: an upper anchor implant member having screw-receiving apertures, a lower anchor implant member having screw-receiving apertures and at least one bridging implant member having screw-receiving apertures; wherein said at least one bridging implant member is connected to said upper anchor implant member by a first mechanical fastener and is connected to said lower anchor implant member by a second mechanical fastener, whereby relative movement between said upper anchor implant member, said lower anchor implant member and said at least one bridging member is precluded. Furthermore, such an assembly wherein said first mechanical fastener is disposed in one of said upper anchor implant member screw-receiving apertures and one of said bridging implant member screw-receiving apertures, and wherein said second mechanical fastener is disposed in one of said lower anchor implant member screw-receiving apertures and another of said at least one bridging implant member screw-receiving apertures; wherein said upper anchor implant member is configured to correspond to an upper segment of a human maxilla and said lower anchor implant member is configured to correspond to a lower segment of a human maxilla; wherein said at least one bridging implant member is configured to maintain said lower anchor implant member in a chosen post-osteotomy orientation and position relative to said upper anchor implant member; wherein said at least one bridging implant member is a post-osteotomy bridging implant member, and wherein said assembly further comprises at least one pre-osteotomy bridging implant member having screw-receiving apertures, wherein said at least one pre-osteotomy bridging implant member is adapted to be removably connected to said upper anchor implant member and said lower anchor implant member, whereby relative movement between said upper anchor implant member, said lower anchor implant member and said at least one pre-osteotomy bridging member is precluded; wherein said first mechanical fasteners is disposed in one of said upper anchor implant member screw-receiving apertures and one of said pre-osteotomy bridging implant member screw-receiving apertures, and wherein said second mechanical fastener is disposed in one of said lower anchor implant member screw-receiving apertures and another of said at least one pre-osteotomy bridging implant member screw-receiving apertures; wherein said upper anchor implant member is configured to correspond to an upper segment of a human maxilla and said lower anchor implant member is configured to correspond to a lower segment of a human maxilla; wherein said at least one pre-osteotomy bridging implant member is configured to maintain said lower anchor implant member in a chosen pre-osteotomy orientation and position relative to said upper anchor implant member; wherein said post-osteotomy bridging implant member is configured to maintain said lower anchor implant member in a chosen post-osteotomy orientation and position relative to said upper anchor implant member; wherein with said pre-osteotomy bridging implant member removed from said upper anchor implant member and from said lower anchor implant member and with said post-osteotomy bridging implant connected to said upper anchor implant member said lower anchor implant, said post-osteotomy bridging implant member maintains said lower anchor implant member in a chosen post-osteotomy orientation and position relative to said upper anchor implant member, said post-osteotomy orientation and position begin different than said pre-osteotomy orientation and position; wherein said upper anchor implant member, said lower anchor implant member, and said at least one bridging implant member further comprise keyed structures to preclude relative movement between said upper anchor implant member, said lower anchor implant member, and said at least one bridging implant member and/or wherein said upper anchor implant member, said lower anchor implant member, said at least one pre-osteotomy bridging implant member, and said at least one post-osteotomy bridging implant member further comprise keyed structures to preclude relative movement between said upper anchor implant member, said lower anchor implant member, and said at least one pre-osteotomy bridging implant member, and to preclude movement between said upper anchor implant member, said lower anchor implant member, and said at least one post-osteotomy bridging implant member.

Alternatively, a maxillofacial orthognathic fixation implant assembly adapted for affixing a lower maxilla segment to an upper maxilla segment after an osteotomy, the assembly comprising: an upper anchor implant member having screw-receiving apertures, a lower anchor implant member having screw-receiving apertures and at least one bridging implant member having screw-receiving apertures; wherein said upper anchor implant member is configured to correspond to and is mountable onto an upper maxilla segment and said lower anchor implant member is configured to correspond to and is mountable a lower maxilla segment;

wherein said at least one bridging implant member is connected to said upper anchor implant member by a first mechanical fastener and is connected to said lower anchor implant member by a second mechanical fastener, whereby relative movement between said upper anchor implant member, said lower anchor implant member and said at least one bridging member is precluded; and wherein said at least one bridging implant member is configured to maintain said lower anchor implant member and said lower maxilla segment in a chosen post-osteotomy orientation and position relative to said upper anchor implant member and said upper maxilla segment. Furthermore, such an assembly wherein said first mechanical fastener is disposed in one of said upper anchor implant member screw-receiving apertures and one of said bridging implant member screw-receiving apertures, and wherein said second mechanical fastener is disposed in one of said lower anchor implant member screw-receiving apertures and another of said at least one bridging implant member screw-receiving apertures; wherein said at least one bridging implant member is a post-osteotomy bridging implant member, and wherein said assembly further comprises at least one pre-osteotomy bridging implant member having screw-receiving apertures, wherein said at least one pre-osteotomy bridging implant member is configured to maintain said lower anchor implant member in a chosen pre-osteotomy orientation and position relative to said upper anchor implant member, and wherein said at least one pre-osteotomy bridging implant member is adapted to be removably connected to said upper anchor implant member and said lower anchor implant member, whereby relative movement between said upper anchor implant member, said lower anchor implant member and said at least one pre-osteotomy bridging member is precluded; wherein said at least one pre-osteotomy bridging implant member is configured to maintain said lower anchor implant member and a lower maxilla segment in a chosen pre-osteotomy orientation and position relative to said upper anchor implant member and an upper maxilla segment, and wherein said post-osteotomy bridging implant member is configured to maintain said lower anchor implant member in a chosen post-osteotomy orientation and position relative to said upper anchor implant member; wherein with said pre-osteotomy bridging implant member removed from said upper anchor implant member and from said lower anchor implant member and with said post-osteotomy bridging implant connected to said upper anchor implant member said lower anchor implant, said post-osteotomy bridging implant member maintains said lower anchor implant member in a chosen post-osteotomy orientation and position relative to said upper anchor implant member, said post-osteotomy orientation and position begin different than said pre-osteotomy orientation and position; and/or wherein said upper anchor implant member, said lower anchor implant member, said at least one pre-osteotomy bridging implant member, and said at least one post-osteotomy bridging implant member further comprise keyed structures to preclude relative movement between said upper anchor implant member, said lower anchor implant member, and said at least one pre-osteotomy bridging implant member, and to preclude movement between said upper anchor implant member, said lower anchor implant member, and said at least one post-osteotomy bridging implant member.

DETAILED DESCRIPTION OF THE INVENTION

In general, the invention is a maxillofacial orthognathic fixation implant assembly and its method of production and use, the implant assembly having an upper anchor implant member, a lower anchor implant member and at least one bridging implant member, the anchor implant members being adapted to be securely mounted to a human maxilla and the at least one bridging implant member being adapted to connect the upper anchor implant member to the lower anchor implant member in a fixed and rigid manner such that relative movement of the two anchor implant members and joined segments of the maxilla is precluded. With the anchor implant members affixed to the maxilla and the maxilla surgically separated between the upper and lower anchor implant members to create a lower portion detached an upper portion, the at least one bridging implant member is connected between the upper and lower anchor implant members to secure and maintain the lower portion of the maxilla in a desired post-operative position relative to the upper portion of the maxilla. The size and configuration of the implant members is determined using 3-D imaging to create a virtual pre-operative model of the maxilla, which is then manipulated through software to produce a desired post-operative configuration model of the maxilla.

FIGS. 1 through 4 illustrate representative embodiments of an upper anchor implant member 21, a lower anchor implant member 22 and a bridging implant member 23, which when assembled in combination define the complete fixation implant 20. The fixation implant 20 is composed of rigid members 21/22/23 formed of biocompatible metal, ceramic or other suitable material which may be safely affixed to human tissue. The upper anchor implant members 21, lower anchor implant members 22 and bridging or cross-brace implant members 23 are provided with screw-receiving apertures 24 to receive mechanical fasteners 25/26, such as biocompatible bone screws, suitable for insertion into bone. The implant upper anchor implant member 21 and implant lower anchor implant member 22 are sized and configured such that at least their inner surfaces, the surfaces which abut the maxilla tissue when the anchor implant members 21/22 are mounted onto the maxilla 10, substantially conform to and match the surface configuration of the maxilla 10 in the areas where anchor implant members 21/22 contact the maxilla surface. The anchor implant members 21/22 are 3-dimensional and may bend, curve or twist in order to match the surface configuration of the maxilla 10. The configuration of the anchor implant members 21/22 may vary, but preferably they are structured to be generally elongated and relatively thin. The upper anchor implant member 21 may and will likely have a different configuration from the lower anchor implant member 22 due to the particular maxilla morphology at differing locations. Furthermore, the right-side and left-side upper anchor implant members 21 may and will likely have different configurations and conformations, and the right-side and left-side lower anchor members 22 may and will likely have different configurations and conformations. The location and number of the screw-receiving apertures 24 may vary.

The bridging implant members 23 typically will not contact the maxilla 10. The bridging implant members 23 extend between and are connected to the anchor implant members 21/22. The bridging implant members 23 are sized and configured such that once joined to the anchor implant member 21/22, the position of the anchor implant members 21/22 will be fixed and maintained with no relative movement of all the implant members able to occur, and such that the desired post-osteotomy relationship of the maxilla segments (i.e., the lower and upper maxilla segments 11/12) formed by the osteotomy is rigidly maintained. Thus, the bridging implant members 23 may be configured such that the lower anchor implant members 22 are translated forward, translated rearward, shifted laterally, rotated, etc., in relation to their prior position relative to the upper anchor implant members 21 after the lower maxilla segment 11 has been separated from the upper maxilla segment 12, In other words, whereas the upper and lower anchor implant members 21/22 are primarily configured to mate with the surface of the maxilla at a predetermined location, the bridging implant members 23 are primarily configured for post-osteotomy positioning of the maxillary segments.

Figure 1:
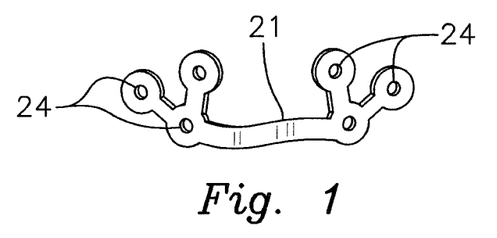
FIG. 1 is an illustration of a representative embodiment of an upper anchor implant member suitable for use on the upper portion of the maxilla.
Figure 2:
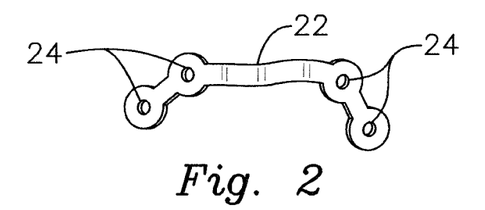
FIG. 2 is an illustration of a representative embodiment of a lower anchor implant member suitable for use on the lower portion of the maxilla.
Figure 3:
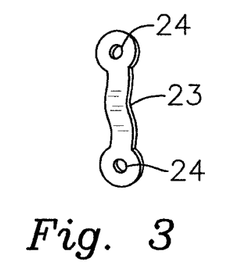
FIG. 3 is a front view of a representative embodiment of a bridging implant member.
Figure 4:
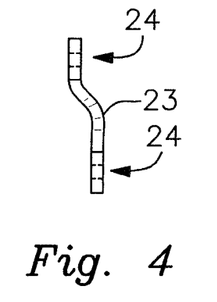
FIG. 4 is a side view of the bridging implant member of FIG. 3.
Figure 5:
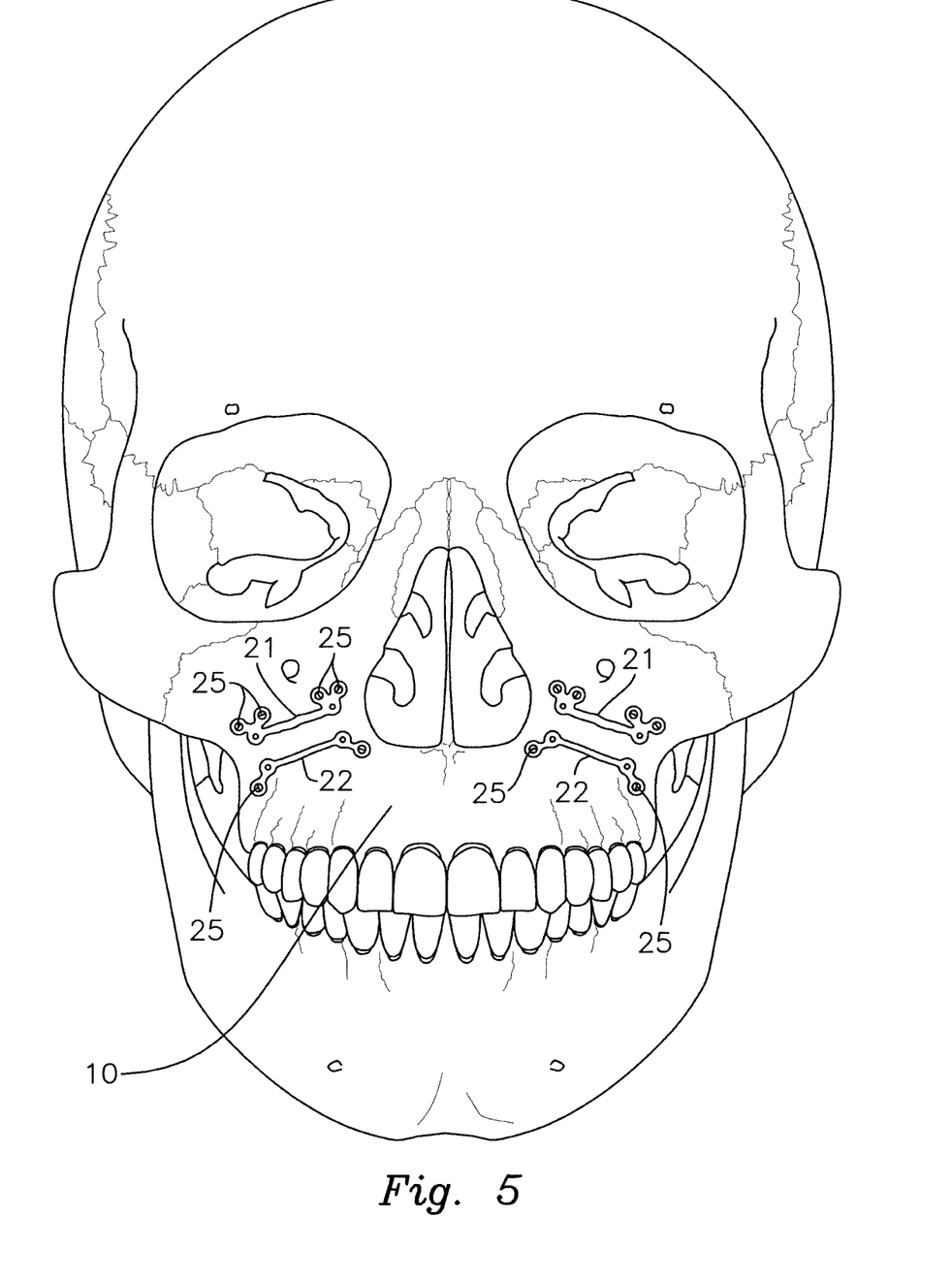
FIG. 5 is an illustration of a skull showing the upper anchor implant members and the lower anchor implant members affixed to the maxilla prior to an osteotomy being performed.
Figure 6:
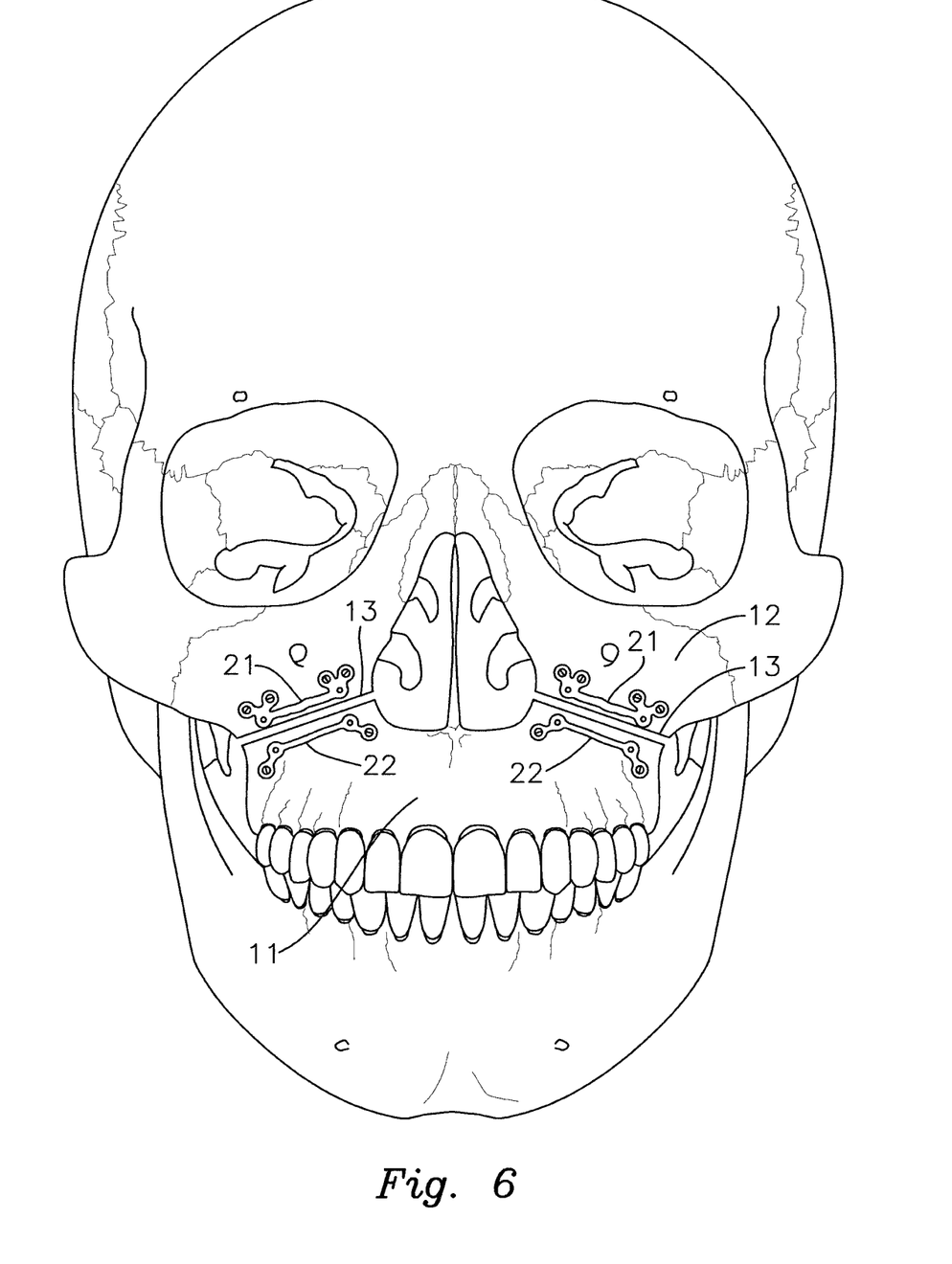
FIG. 6 is an illustration of the skull of FIG. 5 showing the lower portion of the maxilla separated and distanced from the upper portion of the maxilla after the osteotomy has been performed.
Figure 7:
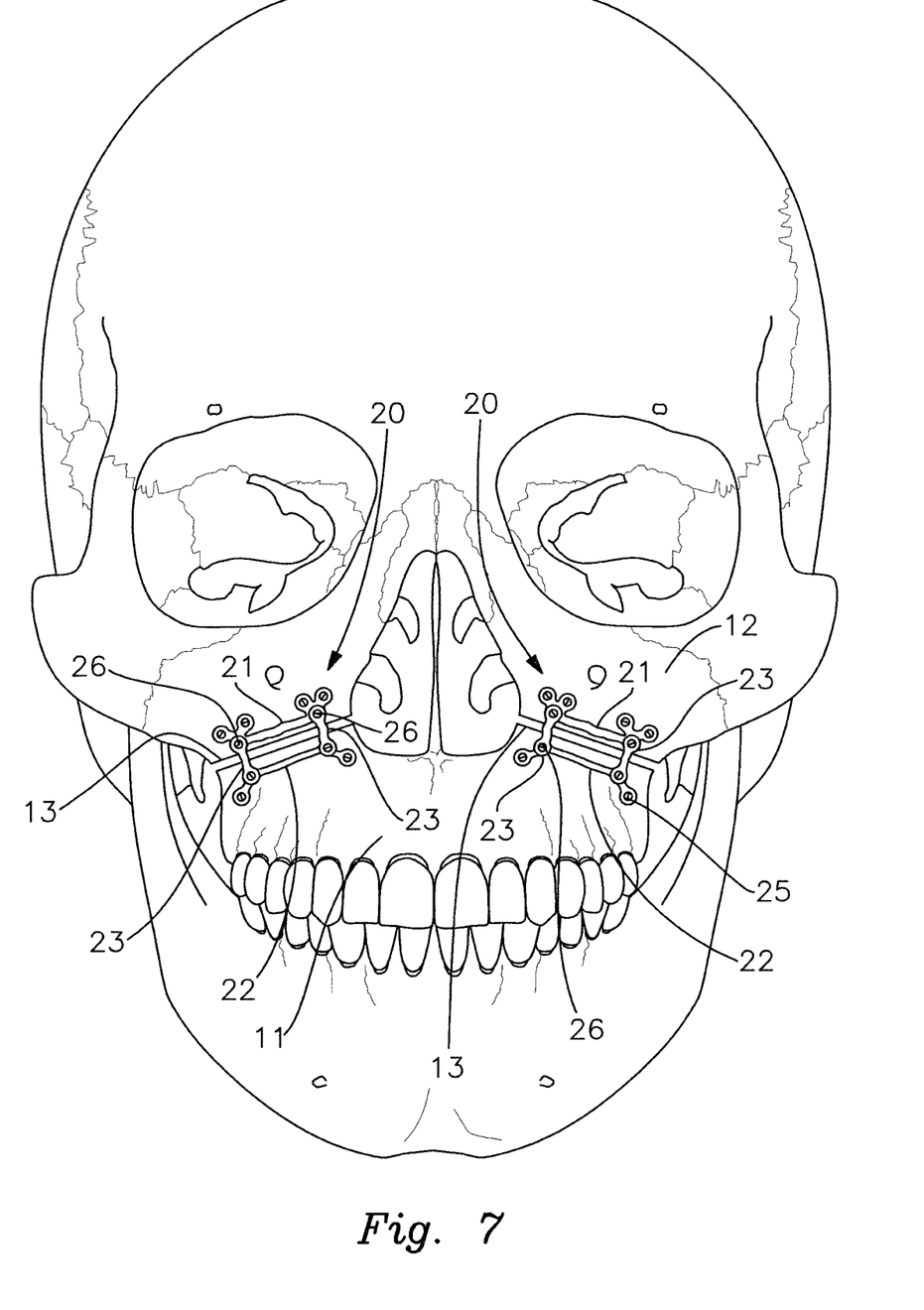
FIG. 7 is an illustration of the skull of FIG. 6 showing the bridging implant members connecting the upper and lower anchor implants, the bridging implant members extending across an osteotomy gap and rigidly maintaining the lower portion of the maxilla in the desired post-operative alignment relative to the upper portion of the maxilla.

As shown in FIG. 7, in a preferred embodiment of the implant 20 there are two bridging implant members 23 for each paired upper anchor implant member 21 and lower anchor implant member 22. The bridging implant members 23 are preferably structured such that an upper aperture 24 in a bridging implant member 23 aligns with an aperture 24 in an upper anchor implant member 21 and a lower aperture 24 in the bridging implant member 23 aligns with an aperture 24 in a lower anchor implant member 22. In this manner bridging implant member mechanical fasteners 26 may be used to connect the bridging implant members 23 to the anchor implant members 21/22. The bridging implant member mechanical fastener 26 may extend through the apertures 24 in the anchor implant members 21/22 and penetrate the maxilla 10, in which case the bridging implant member mechanical fasteners 26 act in similar manner to the anchor implant member mechanical fasteners 25 securing the anchor implant members 21/22 to the maxilla tissue.

Figure 15:
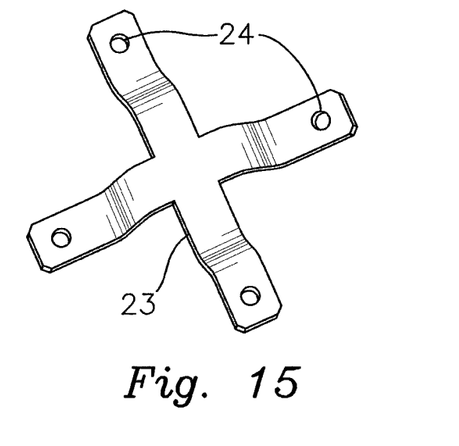
FIGS. 15-17 show alternative embodiments of bridging implant members.
Figure 16:
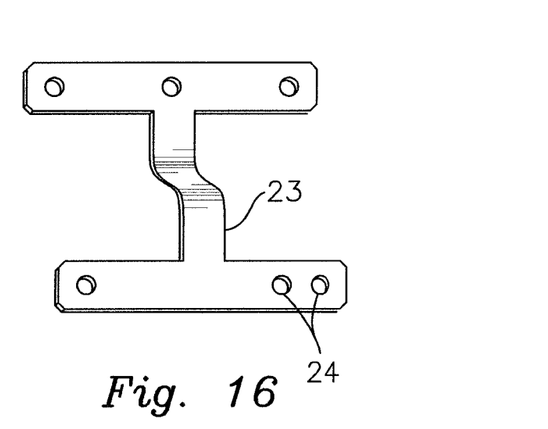
Figure 17:
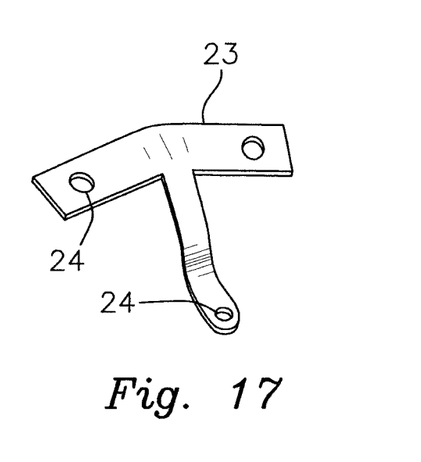

Two or more bridging implant members 23 are preferred for each pair of connected anchor implant members 21/22, as this results in a more rigid structural frame for the implant assembly 20, but other configurations may be suitable. Alternatively, a bridging implant member 23 may be designed in an X-shaped, I-shaped or T-shaped configuration (FIGS. 15-17) or other such configurations for example, wherein the upper and lower ends of the bridging implant member 23 are each provided with at least two apertures 24 to prevent rotational or other relative movement of the assembled members 21/22/23 of the implant 20. Furthermore, while the embodiment shown in the drawings connects the bridging implant members 23 to the anchor implant members 21/22 with bone screw mechanical fasteners 26, the members could be joined by mechanical interlocking structures or bonding means, alone or in combination with the mechanical fasteners 26.

Figure 8:
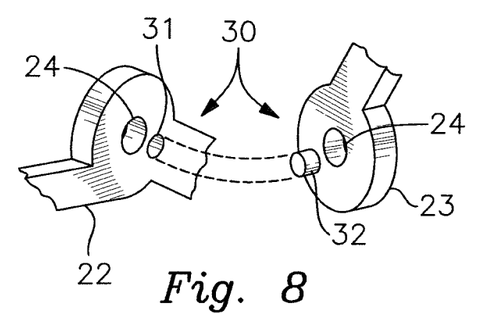
FIG. 8 illustrates a representative embodiment wherein the anchor implant member and the bridging implant member are provided with a keying structure to prevent relative movement once the members are connected using a mechanical fastener.
Figure 9:
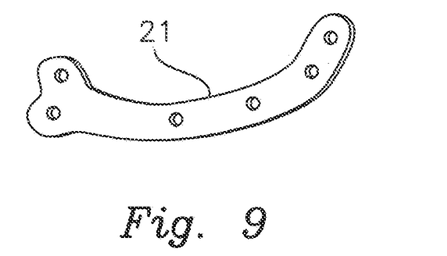
FIG. 9 shows an alternative configuration for the upper anchor implant member.
Figure 10:
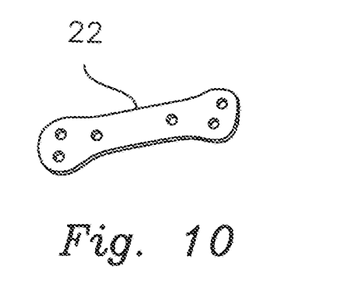
FIG. 10 shows an alternative configuration for the lower anchor implant member.

As the members of the implant 20 are designed such that the lower maxilla segment 11 is maintained in the chosen position and orientation relative to the upper maxilla segment 12 once the implant 20 is assembled, it is preferred that the interfaces or abutting surfaces between the bridging implant member 23 and the upper anchor implant member 21 and the bridging implant member 23 and the lower anchor implant member 22 be provided with movement-inhibiting keyed structures 30 or the like such that when connected the keyed structures 30 preclude angular movement between the connected members 21/22/23. For example, as shown in FIG. 8, the lower anchor implant member 23 may be provided with a bore 31 and the bridging implant member 23 may be provided with a post 32 that fits into the bore 31 when the members 22 and 23 are connected using a mechanical fastener 26. Other configurations for the keyed structures 30, such as slots and tabs, alternating ridges or teeth, or the like may also be utilized to accomplish the result.

A preferred method of utilizing the implant assemblies 20 as described above comprises the steps of creating via software, processor means and a visible monitor a 3-D virtual pre-operative model of the patient's skull that includes the maxilla 10. The surgeon than manipulates the virtual model by creating a virtual osteotomy to separate the maxilla into a virtual lower maxilla and a virtual upper maxilla, and then repositions the virtual lower maxilla relative to the virtual upper maxilla until the desired post-operative relationship is attained. The surgeon then creates virtual implant members, the virtual upper and lower anchor implant members conforming to the surface configuration of the maxilla at the selected affixation location for precise attachment. The surgeon further creates virtual bridging implant members to connect the virtual upper and lower anchor implant members such that the desired relative positions and orientations of the maxilla segments 11/12 will be maintained when the surgery is performed. Actual implant members 21/22/23 are then manufactured to the specifications of the virtual implant members.

To accomplish the surgical procedure, and with the actual implant members 21/22/23 at hand, the surgeon attaches the upper anchor implant members 21 and the lower anchor implant members 22 to the patient's maxilla using anchor implant member mechanical fasteners 25. The osteotomy cut 13 is then made between the upper anchor implant members 21 and the lower anchor implant members 22 to free the lower maxilla segment 11 from the upper maxilla segment 12. The lower maxilla segment 11 is repositioned and the bridging implant members 23 are attached across the osteotomy gap 13 to the pair of corresponding upper anchor implant members 21 and lower anchor implant members 22. Because the implant members 21/22/23 of the implant assembly have been designed based on the 3-D modeling, the configuration of the bridging implant members 23 establishes and maintains the lower maxilla segment 11 in the desired post-operative position relative to the upper maxilla segment 12 once the implant assembly 20 has been fully assembled and secured.

Alternatively, the method may be varied such that only the upper anchor implant members 21 are implanted, the osteotomy cut 13 is performed, and then the lower anchor implant members 22 are attached. Alternatively still, the lower anchor implant members 22 may be implanted first, the osteotomy cut 13 performed, and the upper anchor implant members 21 then attached.

In an alternative embodiment shown in FIGS. 9-12, virtual upper and lower anchor implant members are created in the 3-D virtual model of the patient's maxilla. Virtual pre-osteotomy bridging implant members are then created. After creation of the virtual osteotomy and manipulation, virtual post-osteotomy bridging implant members are created such that the desired relative positions and orientations of the maxilla segments 11/12 will be maintained when the surgery is performed. Actual pre-osteotomy bridging implant members 36A and actual post-osteotomy bridging implant members 36B are then manufactured to the specifications of the virtual implant members.

Figure 11:
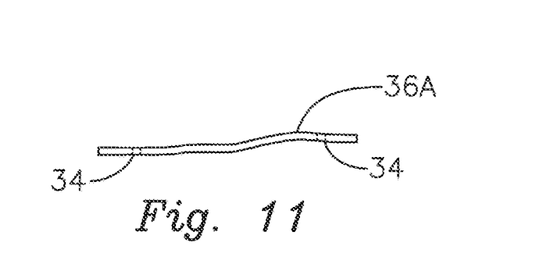
FIG. 11 shows a side view of a pre-osteotomy bridging implant member adapted to temporarily connect and fix the upper and lower anchor implant members in the pre-osteotomy configuration.
Figure 12:
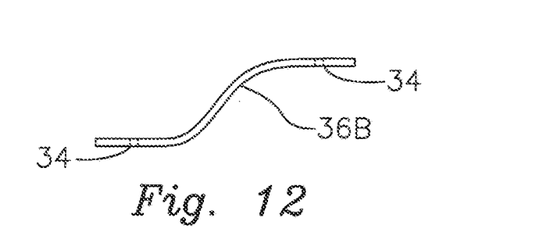
FIG. 12 shows a side view of a post-osteotomy bridging implant member adapted to connect and fix the upper and lower anchor implant members in the post-osteotomy and translated configuration.

In this method, one or more pre-osteotomy bridging implant members 36A with screw-receiving apertures 34 are temporarily attached to the upper and lower anchor implant members 21/22 to form a rigid implant assembly 20 prior to affixation of any member of the implant assembly 20 to the bone, the pre-osteotomy bridging implant member 36A being a temporary alignment member that is configured based on the pre-osteotomy configuration of the maxillofacial area for proper placement of the anchor implant members 21/22 prior to making the osteotomy cut. Once the anchor implant members 21/22 are affixed to the bone, the pre-osteotomy bridging implant member 36A is removed, the osteotomy cut is performed and one or more post-osteotomy bridging implant members 36B are affixed between the anchor implant members 21/22, the post-osteotomy bridging implant members 36B being configured based on the translated post-operative configuration of the maxillofacial area.

Figure 13:
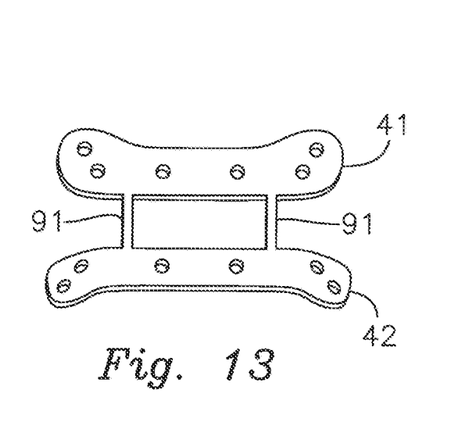
FIG. 13 shows an alternative embodiment wherein the upper and lower anchor implant members are joined by removable connecting members for properly aligning the anchor implant members in the pre-osteotomy configuration.
Figure 14:
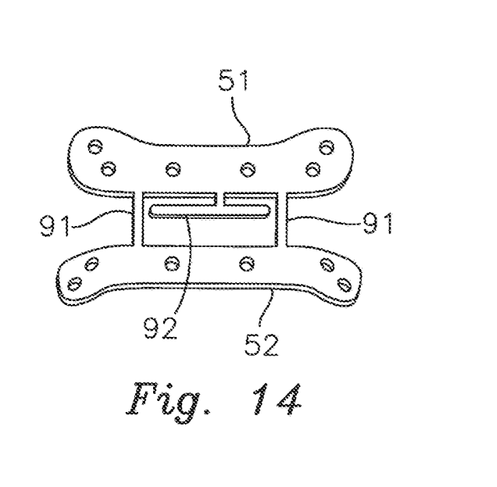
FIG. 14 shows an alternative embodiment wherein the upper and lower anchor implant members are joined by removable connecting members for properly aligning the anchor implant members in the pre-osteotomy configuration and a removable cutting or marking guide is connected to one of the anchor implant members.

In another embodiment shown in FIG. 13, the upper and lower anchor implant members 41/42 are initially formed with one or more thin connecting members 91 extending between the two, such that proper positioning of the anchor implant members 41/42 on the maxilla 10 is easier to achieve. After the anchor implant members 41/42 are attached to the bone, the connecting members 91 are cut and removed. Furthermore, as shown in FIG. 14, a marking or cutting guide 92 may be affixed to one of the anchor implant members 51/52 by a thin connecting member, whereby marking or cutting guide 92 may be utilized to properly locate the osteotomy cut before or after separating the anchor implant members 51/52, the guide 92 being removed after its use.

It is understood and contemplated that equivalents and substitutions for certain elements and steps set forth above may be obvious to those of skill in the art, and therefore the true scope and definition of the invention is to be as set forth in the following claims.

We claim:
1. A maxillofacial orthognathic fixation implant assembly comprising:
an upper anchor implant member having screw-receiving apertures, a lower anchor implant member having screw-receiving apertures and at least one bridging implant member having screw-receiving apertures;
wherein said at least one bridging implant member is connected to said upper anchor implant member by a first mechanical fastener and is connected to said lower anchor implant member by a second mechanical fastener, whereby relative movement between said upper anchor implant member, said lower anchor implant member and said at least one bridging member is precluded;
wherein said at least one bridging implant member is a post-osteotomy bridging implant member, and wherein said assembly further comprises at least one pre-osteotomy bridging implant member having screw-receiving apertures, wherein said at least one pre-osteotomy bridging implant member is adapted to be removably connected to said upper anchor implant member and said lower anchor implant member, whereby relative movement between said upper anchor implant member, said lower anchor implant member and said at least one pre-osteotomy bridging member is precluded;
wherein said first mechanical fastener is disposed in one of said upper anchor implant member screw-receiving apertures and one of said pre-osteotomy bridging implant member screw-receiving apertures, and wherein said second mechanical fastener is disposed in one of said lower anchor implant member screw-receiving apertures and another of said at least one pre-osteotomy bridging implant member screw-receiving apertures;
wherein said upper anchor implant member is configured to correspond to an upper segment of a human maxilla and said lower anchor implant member is configured to correspond to a lower segment of a human maxilla;
wherein said at least one pre-osteotomy bridging implant member is configured to maintain said lower anchor implant member in a chosen pre-osteotomy orientation and position relative to said upper anchor implant member;
wherein said post-osteotomy bridging implant member is configured to maintain said lower anchor implant member in a chosen post-osteotomy orientation and position relative to said upper anchor implant member;
wherein with said pre-osteotomy bridging implant member removed from said upper anchor implant member and from said lower anchor implant member and with said post-osteotomy bridging implant connected to said upper anchor implant member said lower anchor implant, said post-osteotomy bridging implant member maintains said lower anchor implant member in a chosen post-osteotomy orientation and position relative to said upper anchor implant member, said post-osteotomy orientation and position being different than said pre-osteotomy orientation and position.

2. The assembly of claim 1, wherein said upper anchor implant member, said lower anchor implant member, and said at least one bridging implant member further comprise keyed structures to preclude relative movement between said upper anchor implant member, said lower anchor implant member, and said at least one bridging implant member.

3. The assembly of claim 1, wherein said at least one pre-osteotomy bridging implant member, and said at least one post-osteotomy bridging implant member further comprise keyed structures to preclude relative movement between said upper anchor implant member, said lower anchor implant member, and said at least one pre-osteotomy bridging implant member, and to preclude movement between said upper anchor implant member, said lower anchor implant member, and said at least one post-osteotomy bridging implant member.

4. A maxillofacial orthognathic fixation implant assembly adapted for affixing a lower maxilla segment to an upper maxilla segment after an osteotomy, the assembly comprising:
an upper anchor implant member having screw-receiving apertures, a lower anchor implant member having screw-receiving apertures and at least one bridging implant member having screw-receiving apertures;
wherein said upper anchor implant member is configured to correspond to and is mountable onto an upper maxilla segment and said lower anchor implant member is configured to correspond to and is mountable a lower maxilla segment;
wherein said at least one bridging implant member is connected to said upper anchor implant member by a first mechanical fastener and is connected to said lower anchor implant member by a second mechanical fastener, whereby relative movement between said upper anchor implant member, said lower anchor implant member and said at least one bridging member is precluded;
wherein said at least one bridging implant member is a post-osteotomy bridging implant member, and wherein said assembly further comprises at least one pre-osteotomy bridging implant member having screw-receiving apertures, wherein said at least one pre-osteotomy bridging implant member is configured to maintain said lower anchor implant member in a chosen pre-osteotomy orientation and position relative to said upper anchor implant member, and wherein said at least one pre-osteotomy bridging implant member is adapted to be removably connected to said upper anchor implant member and said lower anchor implant member, whereby relative movement between said upper anchor implant member, said lower anchor implant member and said at least one pre-osteotomy bridging member is precluded; wherein said at least one pre-osteotomy bridging implant member is configured to maintain said lower anchor implant member and a lower maxilla segment in a chosen pre-osteotomy orientation and position relative to said upper anchor implant member and an upper maxilla segment, and wherein said post-osteotomy bridging implant member is configured to maintain said lower anchor implant member in a chosen post-osteotomy orientation and position relative to said upper anchor implant member; and
wherein with said pre-osteotomy bridging implant member removed from said upper anchor implant member and from said lower anchor implant member and with said post-osteotomy bridging implant connected to said upper anchor implant member said lower anchor implant, said post-osteotomy bridging implant member maintains said lower anchor implant member in a chosen post-osteotomy orientation and position relative to said upper anchor implant member, said post-osteotomy orientation and position being different than said pre-osteotomy orientation and position.

5. The assembly of claim 4, wherein said first mechanical fastener is disposed in one of said upper anchor implant member screw-receiving apertures and one of said bridging implant member screw-receiving apertures, and wherein said second mechanical fastener is disposed in one of said lower anchor implant member screw-receiving apertures and another of said at least one bridging implant member screw-receiving apertures.

6. The assembly of claim 5, wherein said upper anchor implant member, said lower anchor implant member, said at least one pre-osteotomy bridging implant member, and said at least one post-osteotomy bridging implant member further comprise keyed structures to preclude relative movement between said upper anchor implant member, said lower anchor implant member, and said at least one pre-osteotomy bridging implant member, and to preclude movement between said upper anchor implant member, said lower anchor implant member, and said at least one post-osteotomy bridging implant member.

7. The assembly of claim 4, wherein said upper anchor implant member, said lower anchor implant member, said at least one pre-osteotomy bridging implant member, and said at least one post-osteotomy bridging implant member further comprise keyed structures to preclude relative movement between said upper anchor implant member, said lower anchor implant member, and said at least one pre-osteotomy bridging implant member, and to preclude movement between said upper anchor implant member, said lower anchor implant member, and said at least one post-osteotomy bridging implant member.

8. The assembly of claim 1, wherein said first mechanical fastener is a bone screw adapted to affix said upper anchor implant member and said at least one bridging implant member to the upper segment of the maxilla, and wherein said second mechanical fastener is a bone screw adapted to affix said lower anchor implant member and said at least one bridging implant member to the lower segment of the maxilla.

9. The assembly of claim 4, wherein said first mechanical fastener is a bone screw adapted to affix said upper anchor implant member and said at least one bridging implant member to the upper maxilla segment, and wherein said second mechanical fastener is a bone screw adapted to affix said lower anchor implant member and said at least one bridging implant member to the lower maxilla segment.

10. A maxillofacial orthognathic fixation implant assembly comprising:
an upper anchor implant member having screw-receiving apertures, a lower anchor implant member having screw-receiving apertures and at least one bridging implant member having screw-receiving apertures;
wherein said at least one bridging implant member is connected to said upper anchor implant member by a first mechanical fastener and is connected to said lower anchor implant member by a second mechanical fastener, whereby relative movement between said upper anchor implant member, said lower anchor implant member and said at least one bridging member is precluded;
wherein said first mechanical fastener and said second mechanical fastener are bone screws adapted to affix said upper anchor implant member, said lower anchor implant member, and said at least one bridging implant member onto a maxilla;

wherein said at least one bridging implant member is a post-osteotomy bridging implant member, and wherein said assembly further comprises at least one pre-osteotomy bridging implant member having screw-receiving apertures, wherein said at least one pre-osteotomy bridging implant member is adapted to be removably connected to said upper anchor implant member and said lower anchor implant member, whereby relative movement between said upper anchor implant member, said lower anchor implant member and said at least one pre-osteotomy bridging member is precluded;

wherein said first mechanical fastener is disposed in one of said upper anchor implant member screw-receiving apertures and one of said pre-osteotomy bridging implant member screw-receiving apertures, and wherein said second mechanical fastener is disposed in one of said lower anchor implant member screw-receiving apertures and another of said at least one pre-osteotomy bridging implant member screw-receiving apertures;

wherein said upper anchor implant member is configured to correspond to an upper segment of a human maxilla and said lower anchor implant member is configured to correspond to a lower segment of a human maxilla;

wherein said at least one pre-osteotomy bridging implant member is configured to maintain said lower anchor implant member in a chosen pre-osteotomy orientation and position relative to said upper anchor implant member;

wherein said post-osteotomy bridging implant member is configured to maintain said lower anchor implant member in a chosen post-osteotomy orientation and position relative to said upper anchor implant member; and wherein with said pre-osteotomy bridging implant member removed from said upper anchor implant member and from said lower anchor implant member and with said post-osteotomy bridging implant connected to said upper anchor implant member said lower anchor implant, said post-osteotomy bridging implant member maintains said lower anchor implant member in a chosen post-osteotomy orientation and position relative to said upper anchor implant member, said post-osteotomy orientation and position being different than said pre-osteotomy orientation and position.

11. The assembly of claim 10, wherein said upper anchor implant member, said lower anchor implant member, said at least one pre-osteotomy bridging implant member, and said at least one post-osteotomy bridging implant member further comprise keyed structures to preclude relative movement between said upper anchor implant member, said lower anchor implant member, and said at least one pre-osteotomy bridging implant member, and to preclude movement between said upper anchor implant member, said lower anchor implant member, and said at least one post-osteotomy bridging implant member.

* * * * *